United States Patent
Pade

(10) Patent No.: US 6,966,801 B2
(45) Date of Patent: Nov. 22, 2005

(54) COMPACT COUPLER PLUG, PARTICULARLY FOR A PLANAR BROADBAND LAMBDA PROBE, HAVING AN INTEGRATED SECONDARY LOCKING

(75) Inventor: Wolfgang Pade, Illingen (DE)

(73) Assignee: Robert Bosch GmbH, Stuttgart (DE)

( * ) Notice: Subject to any disclaimer, the term of this patent is extended or adjusted under 35 U.S.C. 154(b) by 8 days.

(21) Appl. No.: 10/311,497

(22) PCT Filed: Apr. 11, 2002

(86) PCT No.: PCT/DE02/01352

§ 371 (c)(1), (2), (4) Date: Jul. 24, 2003

(87) PCT Pub. No.: WO02/087029

PCT Pub. Date: Oct. 31, 2002

(65) Prior Publication Data

US 2004/0014369 A1 Jan. 22, 2004

(30) Foreign Application Priority Data

Apr. 19, 2001 (DE) ........................ 201 06 749

(51) Int. Cl.[7] ........................................... H01R 13/514
(52) U.S. Cl. ..................................................... 439/752
(58) Field of Search ................................ 439/752, 620, 439/404, 417, 595, 596; 204/424, 425, 426; 324/538

(56) References Cited

U.S. PATENT DOCUMENTS 5,658,445 A * 8/1997 Hafele et al. ............... 204/425
6,050,861 A * 4/2000 Genta et al. ................. 439/752
6,066,008 A * 5/2000 Brantingham et al. ...... 439/752
6,083,057 A * 7/2000 Annecke et al. ............ 439/752
6,116,954 A * 9/2000 Ries ........................... 439/596
6,132,256 A * 10/2000 Morsdorf et al. ........... 439/620
6,482,035 B2 * 11/2002 Okabe et al. ............... 439/596

* cited by examiner

Primary Examiner—Hien Vu
(74) Attorney, Agent, or Firm—Kenyon & Kenyon

(57) ABSTRACT

To make possible a very small and compact embodiment of a coupler plug, especially for use for a planar broadband lambda probe having an adjusting unit, a coupler plug is configured in accordance with the following features:

a coupler plug, especially for a planar lambda probe, made up of a housing, namely a base element and a cover element having a primary locking mechanism;

electrical components, that can be inserted and fixed in the housing; and an adjusting element for a probe, especially a planar broadband lambda probe, which is mounted in the coupler plug or outside the coupler plug, via a further contact element, the cover element additionally having a secondary locking mechanism, that is provided as a fixing element for fixing at least one electrical contact that is inserted in the housing, and this fixing element also has support elements that point to the cover element, the support elements being connected to the interior side of the cover element.

4 Claims, 2 Drawing Sheets

COMPACT COUPLER PLUG, PARTICULARLY FOR A PLANAR BROADBAND LAMBDA PROBE, HAVING AN INTEGRATED SECONDARY LOCKING

FIELD OF THE INVENTION

The present invention relates to a coupler plug, in particular for a planar lambda probe (sensor), made up of

- a housing, namely a base element, and a cover element having a primary locking mechanism,
- electrical components, that can be inserted and fixed in the housing, and
- an adjusting element for a probe, especially a planar broadband lambda probe, which is mounted in the coupler plug or outside the coupler plug via a further contact element.

BACKGROUND INFORMATION

Coupler plugs of the aforementioned type are usually designed for the connection between a cable harness plug and a lambda probe, the connections in the coupler plug being provided for adjustment, signal, and/or heating of the probe. The lambda probe and the lambda control, in connection with three-way catalytic converters, represent today an effective method for cleaning exhaust emissions. The lambda probe, which, for example, can be inserted into an exhaust system, includes a sensor for determining the oxygen content in the exhaust gas.

The residual oxygen content is well suited for use as a measured quantity, and it regulates the air-fuel ratio, because it indicates precisely whether the air-fuel mixture is being completely combusted.

In this context, the lambda probe supplies a voltage signal, which represents the momentary value of the mixture composition and which follows the mixture changes. The fuel supply to the engine is controlled by a carburation system in accordance with the signal from the lambda probe in such a way that a stochiometric air-fuel ratio $\lambda=1$ is achieved. Heated or unheated probes are used in accordance with the design of the exhaust gas system and the conditions in which they are used. Outside the field of motor vehicles other applications of the lambda probe include, e.g., regulating gas motors or oil/gas burners.

In particular, broadband lambda probes are designed in modular form and, in combination with planar technology, facilitate the integration of a plurality of functions. They usually have functional layers, which are made up of a porous protective layer, an external electrode, a sensor film, an internal electrode, a reference gas channel film, an insulation layer, a heating element, a heating film, a resistor or adjustment element, and connection contacts.

Because broadband lambda probes are made up of the combination of a nernet concentration cell (=sensor cell) and a pump cell that transports oxygen ions, it can measure very precisely, not only in the stochiometric point at $\lambda=1$, but also in the lean and rich mixture ranges.

Every probe must be individually adjusted. For this purpose, the probe has a built-in resistor ("mini-hybrid"). The adjustment, which is advantageously performed using a laser beam, is made by properly ablating the resistance layer made up of a ceramic substrate, thereby inducing a change in the resistance, so that an adjustment follows.

One specific embodiment provides for the adjustment unit, i.e., the resistor, to be mounted directly at the probe. A further exemplary embodiment provides for the resistor to be accommodated externally, for example, on a cable harness plug that is coupled to the probe.

To prevent the ingress of humidity, contamination or the like into the coupler plug, and to assure that the appropriate atmosphere prevails within the coupler plug, the cover element has additional seals. Furthermore, pressure equalizer elements are mounted on the housing of the coupler plug. In addition, so-called primary locking mechanisms are also provided on the cover element. They ensure that even when the cable harness plug is subjected to strong vibrations, the cover element is firmly seated in the base element.

In addition, secondary locking elements are provided, which offer additional reliability especially in response to powerful stresses.

One disadvantage of the design of the coupler plug discussed here can be seen, in particular, in that it is necessary to mount secondary locking elements in different working and assembly steps.

In addition, it is necessary to manufacture, in particular, the secondary locking elements in a separate manufacturing process.

SUMMARY OF THE INVENTION

An object of the present invention is to refine an embodiment of the coupler plug that is provided especially for a planar broadband lambda probe, in a way that will facilitate simple and substantially cost-effective manufacturing.

The objective is achieved in that the cover element additionally has a secondary locking mechanism, which is provided as a fixing element to fix at least one electrical contact that is inserted in the housing, and this fixing element also has support elements that point to the cover element and that are connected to the interior side of the cover element.

One essential advantage of the present invention is that the coupler plug is designed to be of small construction, because, due to the compact design, i.e., the insertion of electrical contacts into a base element and the placement of the adjusting element likewise in the coupler plug, the exterior dimensions of the coupler plug, which is advantageously positioned between a cable harness and a lambda probe, are very small.

In addition, it has proven to be advantageous that the coupler plug according to the present invention has only a small number of components. As a result, a cost-effective and efficient manufacturing process is possible.

Because the base element is completely enclosed by the cover element, it is possible, by configuring sealing lips within the cover element, or by configuring seals on the base element, to seal off the interior of the coupler plug, thereby protecting it in particular from water spray and/or contamination.

In addition, this also supports the latching of the cover element to the base element. Advantageously, a first and a second latching mechanism, i.e., a primary and secondary locking mechanism, are provided. The latter is configured such that the cover element has latching arms, which, in the closed state of the cover, contact the base element of the coupler plug and produce a latching there using detents.

The primary locking is achieved in two steps. In a first step, the cover element is latched in such a way that it is held on the base element. By further pressing the cover element in the direction of the base element, the fixing element inserted in the base element is fixedly mounted onto the electrical contact element that is guided in the base element, for example, a flat plug sleeve which is connected to the lambda probe. However, the fixing only takes place in that the fixing element is pressed onto the contact element, so that the contact element and the fixing element achieve a solid bond. In addition, the fixing element is restrained in the base element, i.e., in the fixed state of the contact element, the fixing element can only move in the axial plug direction of the cover. Additionally, on the fixing element, support elements are provided that point away from the fixing element, the support elements extending in the direction of the cover element and being fixedly mounted on the interior side of the cover element. In one preferred exemplary embodiment, the cover element, the support element, and the fixing element constitute a single piece.

In the non-activated state of the secondary locking mechanism, i.e., the non-fixing of the contact element, the fixing element is not properly fixed in position by the flat plug sleeve, so that the cover element is not completely sealed.

This has the advantage that it is possible in a simple way to check, whether a successful contacting and thus a securing of the electrical element to the lambda probe has occurred, and whether the cover element is tightly sealed off from the base element.

On the periphery of the cover element, provision is advantageously made for suspension devices which make it possible to secure the coupler plug on a further part, for example, using a groove-and-tongue joint, or for suspension devices such that electrical leads can be secured at the coupler plug.

The cover element is advantageously made of PBT (polybutylene terephthalt) or a similar material.

A further advantageous exemplary embodiment of the present invention is provided for in that the cover element is made so as to be transparent. In this way, the cover element can be mounted before the adjustment is performed, because, in the case of transparent cover elements, the adjustment can be carried out by a laser beam that penetrates through the cover element.

DETAILED DESCRIPTION

Figure 1:
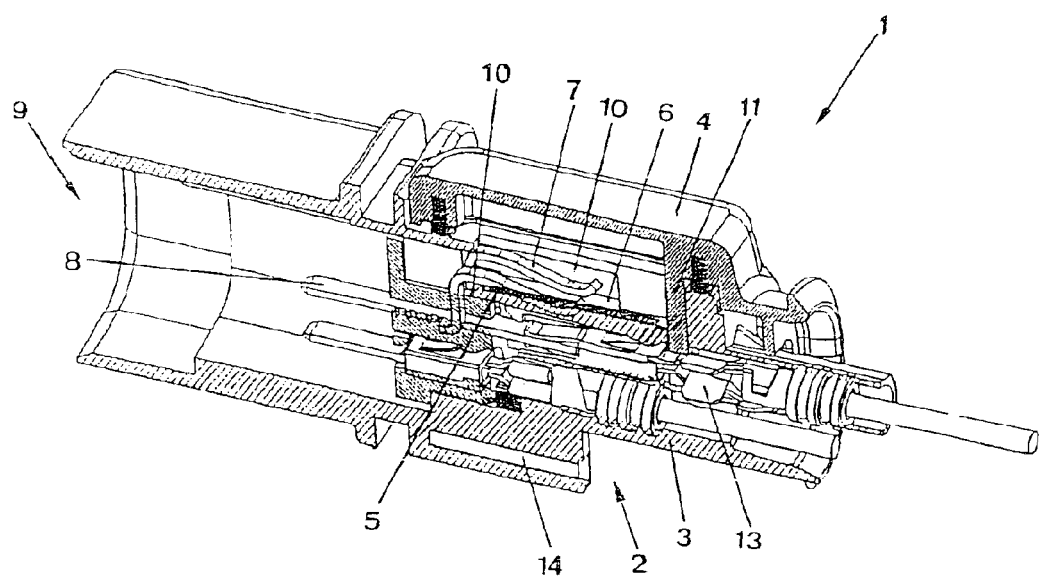
FIG. 1 depicts a perspective view of the coupler plug, in a cutaway view and having a cover that has been placed and mounted.
Figure 2:
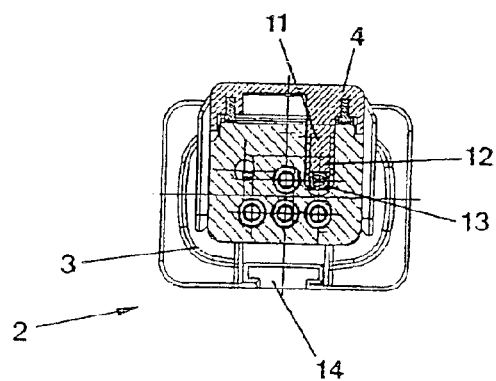
FIG. 2 depicts a cutaway view of the cable harness plug according to FIG. 1, having the cover element in the end position.
Figure 3:
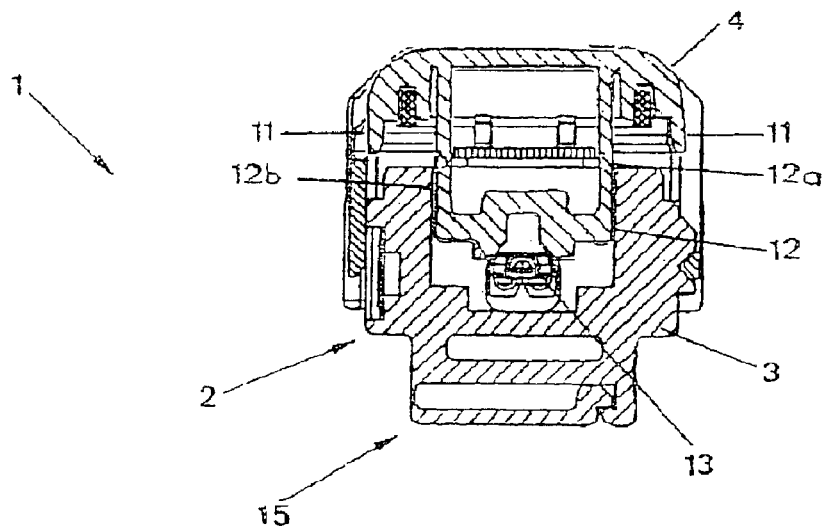
FIG. 3 depicts a cutaway view of a further exemplary embodiment of a cable harness plug according to FIG. 1, having the cover element in the mounted position.
Figure 4:
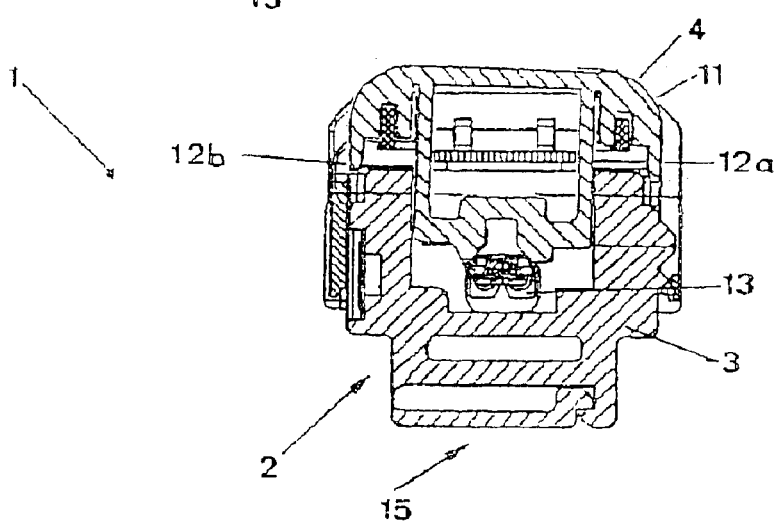
FIG. 4 depicts a cutaway view of a further exemplary embodiment of a cable harness plug according to FIG. 1, having the cover element in an intermediate position, the primary locking mechanism cooperating with the base element.
Figure 5:
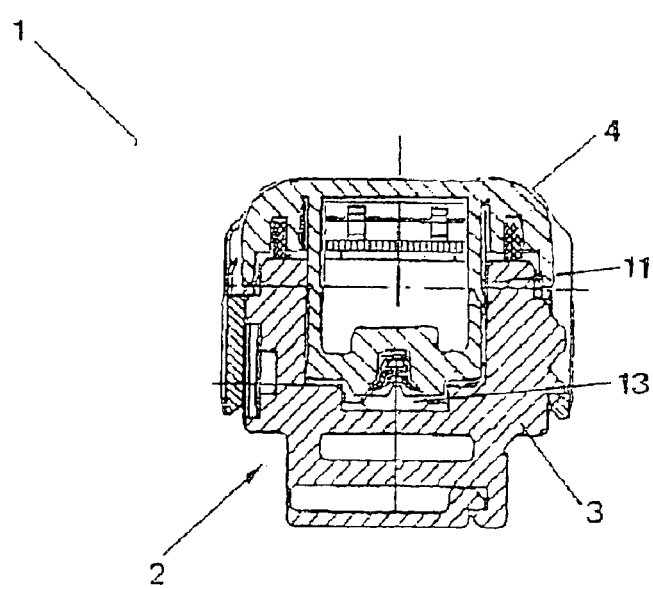
FIG. 5 depicts a cutaway view of a further exemplary embodiment of a cable harness plug according to FIG. 1, having the cover element in the end position.

Coupler plug 1, depicted in FIGS. 1 and 2, as well as the further exemplary embodiment of a coupler plug 1, depicted in FIGS. 3 through 5, is a type of plug that is made up of a housing 2 that is composed of a base element 3 and a cover element 4.

On base element 3, an adjustment unit 6 is mounted in a holding device 5, the adjustment unit in turn being connected via electrical contact elements 7 to the lambda probe that is connected via a connecting element 8, or to the plug that is inserted into coupler plug 1 and is not depicted in greater detail in the drawings.

Electrical contact elements 7 are made up of metal strips that are shaped like printed circuit traces, and have one end extending to the area of coupling potential 9 (FIG. 1) of coupler plug 1.

Adjustment unit 6 is guided by guide elements 10, that are mostly configured on base element 3, and it is held in position by electrical contact elements 7.

To prevent the lateral shifting of adjustment unit 6, support elements 11 are provided perpendicular to the longitudinal extension of adjustment unit 6. These support elements 11, as depicted especially in FIG. 2 and in FIGS. 3 through 5, are configured as part of a fixing element 12.

Fixing element 12 is provided as a secondary locking element and has the function of holding in position an electrical contact 13 that is mounted in housing 2 and that is connected, in particular, to the lambda probe.

For this purpose, fixing element 12 in its cross-section advantageously has a W shape, enclosing electrical contact 13 axially between its two legs 12a/12b in the assembled state (FIGS. 3–5).

Secondary locking element, i.e., fixing element 12, is also configured such that it, along with support elements 11, constitutes a single piece. For this purpose, the free ends of support elements 11 are fixedly bonded to the interior side of cover element 4. In one preferred exemplary embodiment, cover element 4 and support elements 11 form a single piece together with fixing element 12, as is depicted in FIGS. 1 through 5.

In the not yet mounted and fixed state of electrical contact 13, as depicted in FIG. 3, support elements 11 extend far beyond housing 2, such that cover element 4 can only be fixed in a first latching.

The result of this is that when the secondary locking mechanism has not been actuated and therefore electrical contact 13 has not been properly fixed and therefore the positioning of fixing element 12 is not correct, cover element 4 does not close (see FIG. 4).

Only after the secondary locking mechanism is appropriately positioned in its end position is it possible for cover element 4 to adopt its own end position. This position can be achieved very simply by pressing cover element 4 down.

Once it is mounted, the secondary locking mechanism, after being locked, can no longer be detached without completely destroying coupler plug 1.

Advantageously, coupler plug 1 on its periphery has grooves 14 (FIGS. 1 and 2), which permit a coupler plug 1 to be inserted in holders that are provided for this purpose.

In addition, holding and fixing elements 15 are configured in base element 2, as depicted in FIGS. 3–5, the elements making it possible to mount coupler plug 1 on electrical leads.

For this purpose, holding element 15 is configured like a clip, so that coupler plug 1, in the open position of holding element 15, can be plugged into a cable strand, and can then be sealed by a further motion.

In this manner, it is possible to secure the coupler plug, for example, on a motor (holder).

Due to its small exterior dimensions, it is also possible to accommodate the coupler plug in a grooved tube.

What is claimed is:

1. A coupler plug comprising:

a housing including a base element and a cover element having a primary locking mechanism, the cover element further having a secondary locking mechanism, the secondary locking mechanism including a fixing element configured to retain at least one electrical contact inserted in the housing, the fixing element having support elements that project from the cover element, the support elements being connected to an interior side of the cover element;

electrical components adapted to be inserted and fixed in the housing; and an adjusting element for a probe that is mountable either in the coupler plug or outside the coupler plug via a further contact element;

wherein the support elements are configured to prevent lateral shift of the adjusting element;

wherein the coupler plug is a planar broadboard lambda probe;

wherein the adjusting element is a resistor.

2. The coupler plug according to claim 1, wherein the fixing element and the cover element constitute a single piece.

3. The coupler plug according to claim 1, wherein the adjustment element is guided by guide elements.

4. The coupler plug according to claim 3, wherein the guide elements are held in position by electrical contact elements.

* * * * *